Figure 1:
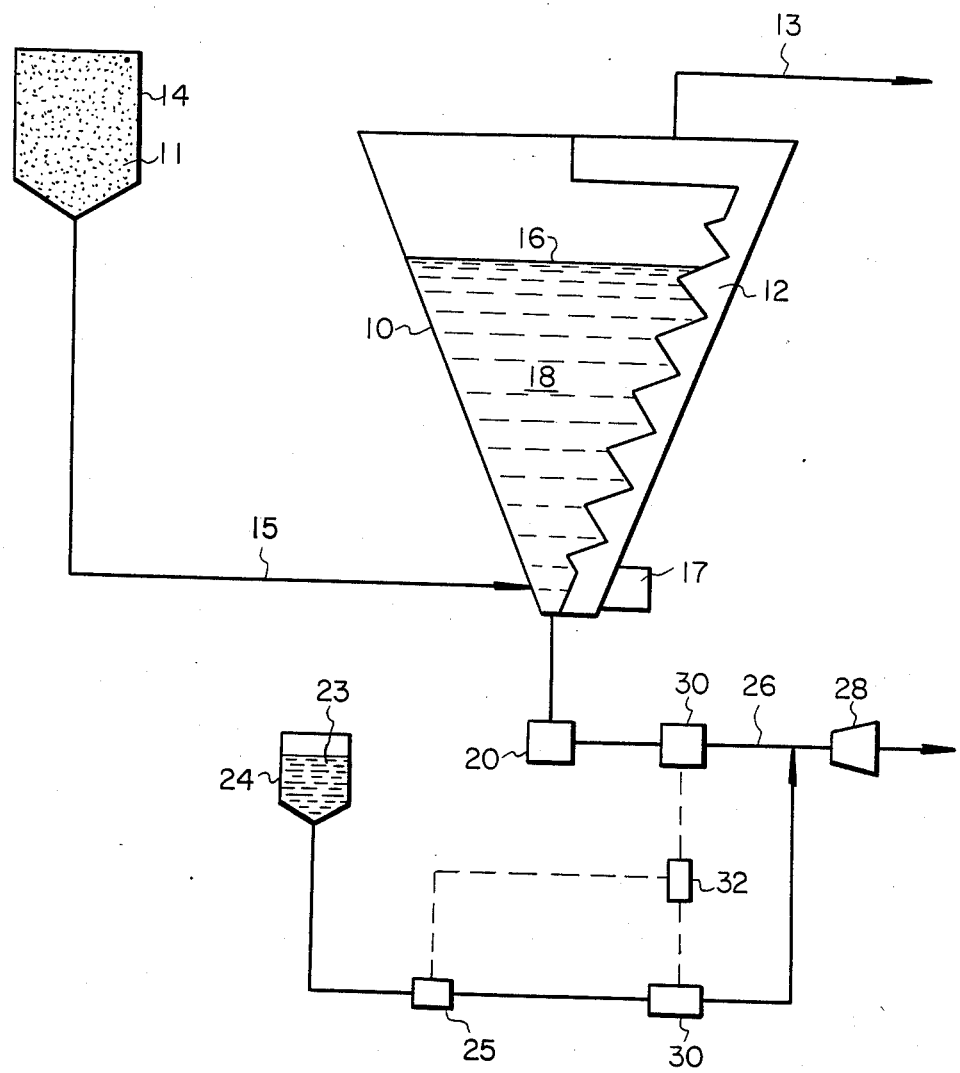

United States Patent [19]

Miles, Jr. et al.

[11] Patent Number: 4,599,363

[45] Date of Patent: Jul. 8, 1986

[54] METHOD FOR WETTING AND DISPERSING POWDERS

[75] Inventors: John J. Miles, Jr., Boonton; Dominick F. DeMasi, Fort Lee, both of N.J.

[73] Assignee: Lever Brothers Company, New York, N.Y.

[21] Appl. No.: 269,303

[22] Filed: Jun. 1, 1981

Related U.S. Application Data

[63] Continuation of Ser. No. 57,242, Jul. 13, 1979, abandoned, which is a continuation of Ser. No. 955,560, Oct. 27, 1978, which is a continuation of Ser. No. 675,440, Apr. 9, 1976.

[51] Int. Cl.$^4$ ............................................. A61K 7/16
[52] U.S. Cl. ........................................ 514/770; 424/49
[58] Field of Search ............................... 424/49–58; 514/770

[56] References Cited

U.S. PATENT DOCUMENTS

| | | | |
|---|---|---|---|
| 2,751,328 | 6/1956 | Saunders | 424/49 |
| 3,109,633 | 11/1963 | Nauta | 259/102 |
| 3,151,847 | 10/1964 | Broomall | 259/129 |
| 3,224,744 | 12/1965 | Broomall | 259/102 |
| 3,272,481 | 9/1966 | Nauta | 259/111 |
| 3,315,947 | 4/1967 | Nauta | 259/111 |
| 3,450,390 | 6/1969 | Nauta | 259/102 |
| 3,551,559 | 12/1970 | Miles | 424/49 |
| 3,602,486 | 8/1971 | Nauta | 259/102 |
| 3,612,492 | 10/1971 | Nauta | 259/102 |
| 3,612,493 | 10/1971 | Nauta | 259/102 |
| 3,659,826 | 5/1972 | Nauta | 259/102 |
| 3,746,314 | 7/1973 | Nauta | 259/21 |
| 3,840,657 | 10/1974 | Norfleet | 424/49 |
| 3,899,159 | 8/1975 | Nauta | 259/21 |
| 3,946,108 | 3/1976 | Tomlinson et al. | 424/49 |
| 3,986,705 | 10/1976 | Nauta | 259/8 |
| 4,020,154 | 4/1977 | Perla | 424/49 |
| 4,069,310 | 1/1978 | Harrison | 424/49 |

OTHER PUBLICATIONS

Riegel Chemical Process Machinery, 2nd Ed. (1953), Reinhold, NY, TP157R 53 (1953), pp. 264–307, "Mixing".

Primary Examiner—Shep K. Rose
Attorney, Agent, or Firm—James J. Farrell

[57] ABSTRACT

A process is provided for the rapid wetting and dispersing of powders suitable for obtaining an essentially gas-free paste, particularly in the manufacture of toothpaste compositions. The process consists of charging a vacuum mixer with the appropriate liquids, and subjecting the liquids to a continuous vacuum that will draw the powders in at the bottom of the mixer in an area of high turbulence generated by a high speed mixing device. The turbulence caused by the expanding air entrained in the powder as it enters the vacuum and generated by the impeller of a high speed mixer, wets the powders very rapidly, inhibits the formation of undesirable lumps, and essentially minimizes loss of powders to the vacuum system. In addition, little or no air is entrained in the resulting paste.

7 Claims, 1 Drawing Figure

METHOD FOR WETTING AND DISPERSING POWDERS

This is a continuation application of Ser. No. 57,242, filed July 13, 1979, abandoned, which is a continuation of Ser. No. 955,560, filed Oct. 27, 1978 which is a continuation of Ser. No. 675,440 filed Apr. 9, 1976.

BACKGROUND OF THE INVENTION

The present process relates to an improvement for obtaining a uniform air-free paste containing a dispersion or solution of substantial amounts of dry insoluble materials in a liquid phase, and more specifically for obtaining an essentially gas-free toothpaste or dental cream.

Dentifrices, such as toothpaste or dental creams are generally extrudable pastes containing insoluble polishing agents and/or abrasives that aid in the removal of plaque, stains and other deposits from the teeth and help to polish them. Due to the physical properties of toothpaste formulations and the nature of the ingredients contained therein, toothpastes will contain a certain amount of entrained air unless suitably prepared. The presence of entrained air in these types of dentifrice formulations generally result in objectionable features in the final product. For example, if a significant amount of entrained air is present the product will not have a homogeneous consistency and appearance, and if a severe and varying amount of air is involved, differences in the final weight for a given container will manifest itself. In the case of translucent toothpastes, the presence of small amounts of air will cause the paste to become opaque.

Air becomes entrained in toothpaste products because of the ingredients and methods that are employed to make up the various formulations. Toothpaste or dental cream formulations contain a variety of constituents, the major class of constituents generally being an insoluble powdered polishing agent and/or abrasive, a bodying agent, a liquid vehicle and a gum stabilizer and/or gelling agent. Other ingredients include flavoring agents and various other constituents for cosmetic, therapeutic or aesthetic effects. The polishing agents or abrasives are generally finely divided water-isoluble powdered materials whose particle size will usually pass through a 140 mesh screen, U.S. Standard Sieve Series.

Toothpastes containing the above-identified class or ingredients can be made up by various and many well-known techniques. One such technique is disclosed in U.S. Pat. No. 3,840,657 issued Oct. 8, 1974 wherein a toothpaste composition is manufactured by making a mixture of a liquid vehicle, gelling agent and polishing agent; degassing this mixture; preparing a second mixture of synthetic organic detergent and liquid vehicle therefor, and degassing this mixture by raising it to an elevated temperature; and finally admixing the first and second mixtures. In the manufacture of toothpastes containing the class of compounds noted above, however, invariably the powdered constituents must be mixed and dispersed with the other liquid ingredients contained in the final toothpaste product. Care must be taken to remove the air in the mixing in of the powders so as to prevent the entrainment of air in the resulting paste.

Various known methods are disclosed in such standard references as "Cosmetics: Science and Technology", by Sagarin, Volume I, pages 510–511, published by Interscience Publishers, Inc. (1972). One such method is the mixing of a paste mass under vacuum to remove the entrained air. The speed of removal will generally depend on the air quantity and mixer construction. Air can also be removed by atmospheric mixing followed by the use of a continuous deaerator such as a Versator available from Cornell Machine Co. The efficiency of deaeration will again be a function of the quantity of air present in the paste mass.

Numerous pieces of equipment are available and capable of achieving a dispersion of solids in liquids. These are essentially mixers containing high speed blades or discs such as a Cowles Dispersall. However, this type of equipment incorporates large quantities of air into the powder-liquid mix. In addition, if the resulting paste mass becomes too thick, insufficient movement occurs and the blade becomes ineffective.

Combination mixers such as an Abbe Dispersall or Eppenbath Agi mixer combine slow speed gate type agitation with a high speed dispersing unit to overcome the above-noted problem of thickened pastes, but still incorporate large quantities of air. Horizontal high speed mixers such as the Day Turbulizer and the Littleford are also effective in wetting down powders, but again, incorporate large quantities of air.

The current practice, therefore, for inhibiting the incorporation of air as the powders are mixed with the liquid constituents, has been to add both liquids then solids to a vacuum mixer followed by sealing of the mixer, evacuating or drawing a vacuum on the contents of the mixer, and then intimately mixing the ingredients to a homogeneous paste. Unfortunately, this procedure has several disadvantages. Generally the full working capacity of the vaccum mixer cannot be utilized since the mixing chamber must contain all of the unwet powders and liquids and be sealed prior to evacation. It will be understood that the volume occupied by the unwetted powders plus liquids invariably exceeds the volume of the resulting finished paste. This is particularly true in toothpaste manufacture where the solids represent 10–60% of the total product and wherein the powders are low in bulk density. The result is that as the powders are added to the mixing chamber, they will have a tendency to remain on top of the liquids, and significant powder losses to the vacuum system can occur. Generally, these low-bulk density powders such as those used in translucent dentifrices must be forced down into the liquids.

Alternatively, if the full working capacity of a vacuum mixer is to be utilized the powders must be added stepwise because the volume of the unwetted powders plus liquids cannot at any time exceed the capacity of the mixing chamber. Such stepwise blending is time consuming and can contribute to powder losses to the vacuum system.

Another problem involved in the wetting out of paste solids using known techniques is that as the powders are taken up in the mixing tank, there is a strong tendency towards lumping when combined with the liquids present therein. Again, if high speed atmospheric mixing is employed, large quantities of air are entrained. On the other hand, if high speed vacuum mixing is employed sufficient headspace must be made available in the mixer to contain all of the unwet powders plus liquids so that the mixer can be sealed before vacuum is drawn and mixing initiated. All of these alternatives involve either excessive entrainment of air, a reduction in mixer capacity or a time-consuming stepwise process, depending on the method used. In the case of the two latter alternatives, powder can be lost to the vacuum system.

In accordance with the present invention, therefore, a method is provided for the rapid wetting and dispersing of difficult to wet insoluble powders or solids for the preparation of paste-type formulations, particulary toothpaste formulations wherein the powders constitute a major portion of the product, while avoiding air entrainment therein. An essentially gas-free paste is obtained by the present method and is a marked simplification of earlier techniques. The method comprises charging the paste liquids to a mixing tank; subjecting the paste liquids to a continuous vacuum and intimate mixing; and introducing the paste powders or solids directly into the paste liquids through the bottom of said mixing tank while maintaining said vacuum and intimate mixing; thereby forming an essentially gas-free paste. It is critical to the process that the vacuum maintained on the mixing tank or paste liquids be of a sufficient level to draw the respective powders or solids into the paste liquids at the bottom of the tank. In effect, the vacuum imposed on the paste liquids is used as the motivating force to convey the powders or solids into the bottom of the mixing tank, thereby creating a wet trap which continuously separates the air from the powders as they are wetted. It will be appreciated that if the vacuum is not continuously maintained, the powders or solids will than have to be added in several stages. Thus, as the powders or solids are pulled into the mixing tank, they are accompanied by entrained air that must constantly be pulled off. This is accomplished by exposing the air in the mixing operation to the constant vacuum and turbulence created by the intimate mixing. Removal of the air will be more efficiently obtained and the powders most effectively dispersed if the powders are introduced into the paste liquids in the area of highest turbulence created by the mixer, which is preferably at the bottom of the mixing tank.

In a preferred embodiment of the invention, an essentially gas-free dentifrice paste is obtained in accordance with the above-defined process by:

(a) introducing a liquid vehicle, which usually include humectants, such as glycerol, liquefied sorbitol (generally a 70% aqueous solution) or other liquid polyols, water, gelling or stabilizing agents, which usually include gums or finely divided hydratable materials such as carboxymethylcellulose and carraghennins and/or flavoring agents and other liquid constituents for their cosmetic, therapeutic or aesthetic effect, to a mixing tank;

(b) subjecting the liquid vehicle to a continuous vacuum and intimate mixing; and (c) introducing insoluble toothpaste solids comprising a polishing agent or abrasive or mixtures thereof, such as silica xerogels, hydrated aluminas and complex alumino silicates; and/or bodying agents, such as silica aerogels or other colloidal silicas having thickening or bodying capacity; into the bottom of said mixing tank while maintaining said vacuum and intimate mixing;

said vacuum being of sufficient level to draw the insoluble toothpaste solids into the liquid vehicle, preferably in the area of highest turbulence at the bottom of the tank.

Once the foregoing homogeneous essentially gas-free dentifrice paste is prepared, which can generally be referred to as a base paste, various other classes of ingredients may be added to finalize the toothpaste product, which generally include a mixture of humectant, such as a polyhydric alcohol, and surface active agent, and any other flavoring agents or ingredients that will finalize the desired toothpaste product. The mixture of humectant and surface active agent solution is degassed and may be added directly to the base paste in the mixing tank, but is preferably degassed and added to the base paste in a closed system downstream of the mixing tank. The surfactant/humectant solution can be made essentially gas free by heating it at atmospheric pressure or under vacuum, or by vacuum degassing. In accordance with the preferred method, the base paste and surfactant solution is withdrawn from their respective containers, and combined into one mixture in a closed system under pressure in the absence of air. By mixing the base paste and detergent solution under pressure in a closed system, entrainment of further air into the toothpaste ingredients is prevented.

Finally, any other essentially gas-free flavoring agents or other constituents may be added to the combined mixtures while pressure and the absence of air is maintained.

The process equipment is shown in the drawing. A mixer tank 10 to contain a liquid medium 18 is provided with a mixing device 12 and a line to a vacuum source 13. The mixing device 12 may optionally be a mixing screw as shown. At least one hopper 14 is supplied for solid material 11. The hopper 14 communicates with the mixer tank 10 through a line 15 at a point below the surface 16 of the liquid medium 18 in the mixing tank 10, in relatively close proximity to the lump breaker 17, at a point where the turbulence is high. The discharge end of the mixing tank 10 is provided with a paste pump 20 to facilitate discharge. A degassed detergent solution 23 containing various adjuvants is placed in a container 24 and injected through an injection pump 25 into a paste discharge line 26. The paste, together with the detergent solution then is passed through an in line mixer 28. To control the amount of detergent solution injected, flow meters 30 and a controller 32 cooperating with the injection pump 25 may be employed.

In operation, the liquid medium 18 is charged to the mixing tank 10. The mixing device 12 and the lump breaker 17 are then activated to mix and create turbulence in the liquid medium 18. A continuous vacuum is obtained in the headspace of the mixing tank 10 by means of the vacuum source 13. The solids 11 contained in the hopper 14 then are drawn into the mixing tank 10 through the line 15 below the surface 16 of the liquid medium 18 and at a point of high turbulence therein. After full delivery of the solids 11 the vacuum and mixing are continued until an essentially gas free paste is formed. The paste is then discharged through the paste pump 20. The detergent solution 23, which may contain other adjuvants as desired, is degassified and placed in the container 24. This solution is then injected into the paste by means of the injection pump 25 at a convenient point in the paste discharge line 26. The solution 23 and paste combination are then passed to the "in line" mixer 28 to form a final paste which is then discharged to bulk storage. The flow meters 30 and the controller 32 may be used to control the amount of the detergent solution 23 injected into the paste.

As will be seen from the examples that follow, highly desirable effects and advantages result from the process according to the invention herein. Because the powders or solids are forced into the paste liquids in an area of high turbulence caused by the action of the mixing device, an unexpected rapid wetting of powders or solids is obtained. In addition, the mixing action is enhanced by the turbulence resulting from the rapidly expanding air entrained in the powders as it enters into an area of decreased pressure.

Another distinct advantage is that lumping of the powders or solids in the paste is markedly decreased due to the rapid expansion of air entrained in the powders or solids, thereby keeping the particles separate so that the discrete particles become wetted, and avoiding agglomerates or lumps. Moreover, minimized air entrainment is obtained since air is continuoulsy being separated from the powders and drawn from the mixer as the vacuum is continuously maintained. Finally, the mixer is utilized to its maximum working capacity since little or no headspace is required to accommodate the unwetted powders or solids.

The polishing agents or abrasives in powdered or solid form mentioned above useful in the preparation of dentifrice pastes in accordance with the instant invention include calcium carbonate, crystalline silica, colloidal silica, complex alumino silicates, aluminum hydroxide (including alpha alumina trihydrate), aluminum oxide, aluminum silicate, dicalcium phosphate dihydrate and silica xerogels. Other polishing agents or abrasives generally will include those described in U.S. Pat. No. 3,840,657 issued Oct. 8, 1974 which polishing agents or abrasives are incorporated herein by reference. It will be noted that other listings of solid or powdered materials of the type encompassed by the present invention are described in the standard handbook, "Cosmetics: Science and Technology", by Sagarin, Second Edition, 1972, published by Interscience Publishers, Inc. which is also incorporated herein by reference. Most of the polishing agents or abrasives described above are useful in the preparation of opaque paste dentifrices but the colloidal silicas, especially the silica xerogels, and complex sodium alumino silicates, may be utilized in the preparation of translucent paste dentifrices.

The complex alumino silicates salts, which appear to contain inter-bonded silica and alumina having Al—O—Si bonds, are described by Tamele in "Chemistry of the Surface and the Activity of Alumina-Silica Cracking Catalysts", appearing in "Discussions of the Faraday Society", No. 8, pages 270–279 (1950). The colloidal silicas used are silica xerogels which are generally described in U.S. Pat. No. 3,538,230 issued Nov. 3, 1970. Appropriate xerogels have been marketed under the trademarks or tradenames of Syloid 63 and Syloid 74 available from the W. R. Grace Company.

The content of polishing agent or abrasive in the final paste product will generally be greater for the opaque toothpastes as opposed to the translucent or transparent dental pastes. For example, in the manufacture of commercially acceptable opaque dental pastes, 20–75% of polishing agent or abrasive will usually be present, preferably from about 30–60%. However, in the manufacture of translucent dental pastes, the content of polishing agent or abrasive is typically from 5–40%, the preferred content being from 5–20%.

It should be noted that the abrasive or polishing agent of a dentifrice paste can be a major contributor to paste body and consistency at levels in excess of 30% by weight of the final product. As this level increases, so will the bodying effect on the paste increase. Conversely, at levels below 30%, such as in translucent dentifrice pastes, the bodying effects of the abrasive or polishing agent will be minimal. Accordingly, bodying agents must be employed to develop suitable paste body and consistency, and may be used, even at the higher levels of abrasive. The level of bodying agent, therefore, will generally be in the range of from 1–20% by weight, preferably from 4–15%.

The bodying agents in accordance with the present invention include colloidal silicas having bodying properties, such as the aerogels Syloid 244 and 266 (available from W. R. Grace Company), Aerosil (available from DeGussa Co.) and pyrogenic silicas sold under the tradename Cab-O-Sils (available from Cabot Corporation). Other bodying agents that may be included with the insoluble toothpaste solids are precipitated silicas having bodying properties, such as Zeosyl 200 and Zeofree 153 (available from Huber Company), Hisil 233 (available from Pittsburgh Plate Glass Company), and Sipernat 22S (available from DeGussa Company). These bodying agents may also function as polishing agents.

The gelling or stabilizing agents that can be used in accordance with the present invention preferably include the natural and synthetic gums and gum-like materials, desirably sodium carboxymethylcellulose, hydroxyethylcarboxymethylcellulose, carrageenin, gum tragacanth, alginates, bentonite and other natural clays and synthetic inorganic clays. The gelling agents utilized are hydratable or gelled with water or alkanols, especially with polyhydric alcohols such as glycerol and sorbitol. Usually the gel or stabilizing agent is formed with al least some water present.

The proportions of gelling or stabilizing agents that will be present in the final dentifrice paste will generally be in the range of from 0.1–20% by weight of the final product and in the case of synthetic gums such as sodium carboxymethylcellulose, the range will preferably be from about 0.1 to 3%.

The liquid vehicle of the dentifrice paste products made in accordance with the instant is generally a humectant/water mixture, and will generally be present in the final paste product in the range of from about 10 to 85% by weight, with from 30–70% being a preferred range for opaque dentifrice pastes, and from 40–85% being preferred for translucent dental pastes. Humectants used in dentifrice formulations are well known in the art and include glycerine, sorbitol, propylene glycol, polyethylene glycol, mannitol, polypropylene glycols, and mixtures thereof.

The water content of the dentifrice paste product will be dictated by the desired characteristics of the final product. For example, translucent dentifrice pastes will contain from about 10–30% water. Any amount above that range will result in a decrease in translucency of the paste. For opaque dentifrice pastes, the water content may range from 5–35%, but will usually be from about 8–30%, preferably from 20–30%.

The surface active agents or synthetic organic detergents that can be employed in the present process for the manufacture of an essentially gas-free dentifrice paste generally include anionic, nonionic, cationic, ampholytic or zwitterionic compounds, or mixtures thereof. The most preferred surface active agents for use in dentifrice paste formulations are sodium lauryl sulfate, alkyl aryl sulfonates such as sodium linear dodecyl benzene sulfonate, and N-lauroyl sarcosine and the sodium, potassium and ethanol amine salts of N-lauroyl-, N-myristoyl- and N-palmitoyl sarcosine. Other suitable surfactant compounds are described in U.S. Pat. No. 3,840,657 and the text "Surface Active Agents", Volume II (1958), by Schwartz, Perry and Berch, which compounds are incorporated herein by reference.

The surface active agents or detergents constitute from 0.5 to 5% of the dentifrice paste in most cases, although slightly higher proportions for detergent or surfactant may be utilized up to as high as 10%.

The flavoring materials employed are largely essential oils but also may include various flavoring aldehydes, esters, alcohols and similar materials known in the art. They will generally be present in a range of from 0.5 to 5.0% by weight of the final paste product.

In addition to flavoring materials, sweetening agents may be present, preferably including sucrose, lactose, maltose, saccharin, and sodium and calcium cyclamates. A preferred sweetening agent is saccharin which will usually be present in an amount of from 0.05–0.5%.

A wide range of adjuvant materials may also be present in the final product which include buffers, preservatives, bactericides, fungicides, therapeutic materials such as fluorine-containing compounds, coloring and whitening agents, dyestuffs, pigments, decorative suspended materials, fillers, lubricants and stabilizers. All these adjuvant materials are generally described in U.S. Pat. No. 3,840,657 which materials are incorporated herein by reference. The proportions of these various materials will be present anywhere from an amount of 0.01 to 1% by weight of the final product.

The following examples will illustrate the invention, but are not to be limited thereby.

EXAMPLE 1

Translucent toothpaste compositions were made according to the process of the invention having the formulas itemized below. Percentages are given on the basis of weight of the final product.

| Ingredients | Toothpaste A % | Toothpaste B % |
|---|---|---|
| Powders | | |
| Syloid 63 (abrasive) | 14.0 | 14.0 |
| Syloid 244 (bodying agent) | 8.0 | 5.0 |
| Zeosyl 200 (bodying agent) | | 3.0 |
| Mucilage | | |
| Sorbitol (70% aqueous solution) | 46.7 | 46.7 |
| Glycerine (95% aqueous solution) | 14.7 | 14.7 |
| Polyethylene glycol | 5.0 | 5.0 |
| Sodium Benzoate | 0.1 | 0.1 |
| Sodium Saccharin | 0.4 | 0.4 |
| Sodium carboxymethylcellulose (gum stabilizer) | 0.3 | 0.3 |
| Water, distilled | 1.4 | 1.4 |
| Detergent Solution | | |
| Glycerin (95% aqueous solution) | 5.6 | 5.6 |
| Sodium lauryl sulfate | 1.4 | 1.4 |
| Ethanol | 0.8 | 0.8 |
| Adjuvants | | |
| Flavor (essential oils) | 1.2 | 1.2 |
| Dye solution | 0.4 | 0.4 |
| | 100.0% | 100.0% |

The above-identified formulations were made up as follows. The mucilage above, including humectant, gum stabilizer, preservative, sweetener and water, were made up in a premix tank at a temperature of between 100°–130° F. and then charged to a Nauta Vacuum Mixer, Model MBX-70 having a 52 gallon working capacity. The flavoring and dye solutions were then combined with the mucilage in the vacuum mixing chamber and mixed by activating the mixer screw and high speed lump breaker. A vacuum of 12 inches of mercury was drawn on the mixing chamber and the above-identified powders were drawn into the mucilage at the bottom of the chamber in an area of close proximity to the lump breaker. The powders were wet out and dispersed into the mucilage within 6 minutes for Toothpaste A and 8 minutes for Toothpaste B.

The vacuum was then increased to and maintained at 27 inches Hg. and mixing continued for 11 minutes for both pastes. The mixer was shut down, the vacuum released, and a smooth, homogeneous, essentially gas-free base paste was obtained.

The above-identified detergent solution, including humectant, was prepared in a separate premix tank and degassified by heating the solution to a temperature of 110°–120° F. The detergent solution was then added to the base paste in the vacuum mixer, vacuumed to 27 inches Hg., and mixing continued for 10 minutes. An essentially gas-free dentifrice paste was obtained for both Toothpastes A and B. The duration of time for the process steps totalled 27 minutes for Toothpaste A and 29 minutes for Toothpaste B.

EXAMPLE 2

The same toothpaste formulations were made up by conventional atmospheric mixing techniques involving basically the same procedures described in Example 1, except that the powders were added to the mucilage through the top of the vacuum mixer and mixed in under atmospheric pressure. The wetting and dispersing of powders into the mucilage required approximately 15 minutes for both Toothpastes A and B; another 15 minutes were expended to develop a homogeneous base paste by operation of the mixing apparatus without the vacuum. The detergent solution was then added to the resulting base paste and mixed for 10 minutes to obtain a complete toothpaste formulation. The total time expended for the process steps was approximately 40 minutes in each case for Toothpastes A and B. It should be noted that this paste required degassing.

It will be understood that the heating of the mucilage to a temperature within the range of 110°–120° F., or more generally from 100°–140° F., is not critical to the process according to the invention, but merely facilitates deaeration or degassing of the resulting paste. In addition, the level of vacuum utilized in accordance with the invention, as noted hereinbefore, should generally be sufficient to draw the powders into the mucilage. The level of vacuum will therefore be dependent on (a) the static head at the point of powder introduction to the mixing chamber, which in turn is dependent on the quantity and density of the mucilage and the design of the mixer, and (b) the desired flow rate of the powders into the mixing chamber. The rate of powder addition will be a function of the powder bulk density and the efficiency of the distribution or mixing in of the powders into the mucilage. It should be understood, therefore, that a person skilled in the art will be able to determine with little difficulty the foregoing parameters that will be advantageous for the manufacture of a desired dentifrice paste.

EXAMPLE 3

A translucent toothpaste composition was made according to the present invention having the following formula:

| Ingredients | Toothpaste C % |
|---|---|
| Powders | |
| Syloid 63 (abrasive) | 10.0 |
| Syloid 244 (bodying agent) | 11.0 |
| Mucilage | |
| Sorbitol (70% aqueous solution) | 40.0 |
| Glycerine (95% aqueous solution) | 15.8 |
| Polyethylene glycol | 5.0 |
| Sodium Benzoate | 0.1 |
| Sodium Saccharin | 0.3 |
| Carrageenin (Viscarin TP-4) | 0.3 |
| KOH (5% aqueous solution) | 0.6 |
| Dye Solution | 0.2 |
| Water distilled | 1.3 |
| Stannous fluoride/Sorbitol solution | 6.0 |
| (0.66%) | |
| NaOH (50% aqueous solution) | 0.3 |
| Detergent Solution | |
| Glycerine (95% aqueous solution) | 5.6 |
| Sodium lauryl sulfate | 1.4 |
| Ethanol | 1.3 |
| Flavor (essential oils) | 0.8 |
| | 100.0% |

The above-identified formulation was prepared as follows. The mucilage was made up in a premix tank at a temperature of 100°–130° F., and charged to a Nauta Vacuum Mixer, Model MBX-70 having a 52 gallon working capacity. The mixer was activated. The NaOH solution was then added to the mucilage followed by the addition of the stannous/fluoride/sorbitol solution and flavor.

A vacuum of 12 inches Hg. was then drawn and maintained on the contents in the mixer, and the toothpaste powders were drawn into the liquid mix through the bottom of the mixer as in Example 1. The time elapsed to wet and disperse the powders into the liquid contents of the mixer was 9 minutes.

The vacuum level was then increased to and maintained at 27 inches Hg., and mixing continued for 20 minutes. The mixer was shut down, the vacuum released, and a smooth, homogeneous essentially gas-free base paste was obtained. The time elapsed for the process steps up to this point was 29 minutes.

The detergent solution above was prepared as in Example 1 and added to the base paste in the vacuum mixer, the total mixture vacuumed to 27 inches Hg., and mixing continued for 10 minutes. The vacuum mixer was shut down and an essentially gas-free toothpaste was obtained. The duration of time for the process steps totalled 39 minutes.

EXAMPLE 4

The same toothpaste formulation in Example 3 was made up by conventional vacuum mixing techniques involving basically the same procedures described in Example 3, except that the powders were added to the liquid mix through the top of the vacuum mixer under atmospheric pressure while the screw and lump breaker was in operation. The time elapsed before a vacuum could be drawn on the mixer contents was 25 minutes.

A vacuum level of 27 inches Hg. was drawn on the mixer, and mixing continued for another 20 minutes. The vacuum mixer was then shut down and an essentially gas-free base paste was obtained. The total time elapsed up to this point was 45 minutes.

The detergent was added to the base paste as in Example 3 and an additional 10 minutes of mixing was required to obtain an essentially gas-free translucent toothpaste composition. The total time expended was 55 minutes as compared with 39 minutes using the method according to Example 3.

EXAMPLE 5

The dentifrice paste formulation identified as Toothpaste C in Example 3 was made up according to the instant invention on a production scale using a Nauta Vacuum Mixer, Model MBX 1225 having a 917 gallon working capacity. The procedure for the preparation of the base paste was the same as that set forth in Example 3 except that owing to the size of the batch made, the amount of time to draw the toothpaste powders into the liquid mix (mucilage) through the bottom of the mixing tank was increased to 28 minutes. The vacuum required to draw in the powders was 20 inches Hg. The subsequent mixing time for the combined liquid mix and powders under an increased vacuum of 27 inches Hg. was 20 minutes. The total time elapsed for the foregoing process steps to obtain an essentially gas-free, homogeneous, base paste was 48 minutes. A summary of these times is set forth in Table 1 below.

The detergent solution was prepared and degassified in a separate tank (as in Example 1).

The base paste was then pumped from the vacuum mixer into a closed continuous proportioning system under a pressure of 50 psig. The detergent solution was combined with the base paste in the proportioning system, which has incorporated therein appropriate metering devices and an in-line mixer, to yield an essentially gas-free, homogeneous translucent toothpaste formulation. The advantage of adding the detergent solution downstream of the vacuum mixer is that degassing of a detergent or surfactant free base paste is decidedly more rapid than if the surfactant were present. The presence of a surface active agent in the base paste acts to stabilize, disperse and emulsify any entrained air bubbles thereby creating a resistance for their removal.

EXAMPLE 6

The dentifrice paste formulation of Example 5 was prepared in the same Nauta Vacuum Mixer, Model MBX 1225 using the same procedure therein, except that the powders were added to the liquid mix via the top of the vacuum mixer under atmospheric pressure. The total time required to disperse and wet the powders was 65 minutes. Subsequent atmospheric mixing was initiated and continued for 10 minutes. The total time elapsed up to this point was 75 minutes.

The detergent solution was combined with the above base paste as in Example 5, and an opaque toothpaste formulation was obtained due to the entrainment of air. Further degassification of the toothpaste was necessary to obtain the desired translucency.

The following table summarizes the advantages of time and increased batch size for Examples 5 and 6 resulting from the method according to the invention herein. It will be noted that the time required for preparing the mucilage and adding the NaOH, stannous fluoride and flavor solutions was the same for both Examples 5 and 6.

TABLE 1

|  | Example 5 time, minutes | Example 6 time, minutes |
|---|---|---|
| Add Powders to Mucilage and Wet Down | 28 | 65 |
| Completion of Mixing of Mucilage and Powders | 20 | 10 |
| Quantity of Base Paste Prepared | 10,100 lbs. | 8,250 lbs. |

It will be seen that significant shortening of time was required to obtain a base paste using the procedure of vacuum mixing combined with wetting and dispersion of the powders according to the invention herein. Moreover, a significant increase in batch size using the above method was realized by the Nauta Mixer because the bulk density or headspace occupied by the unwetted powders introduced via the top of the mixer was not a factor in preparing the base paste. This disadvantageous factor is eliminated by the present invention.

Another advantage of the method according to the invention is that a base paste can be prepared devoid of the various materials such as flavoring and sweetening agents, surface active agents, dyes, and any other adjuvant materials which are used for their cosmetic, therapeutic or aesthetic properties which can be excluded from the vacuum mixer contents. Base paste prepared in this fashion will be capable of being utilized for dentifrice paste compositions having different properties by virtue of adding varying kinds of adjuvant materials noted above, for example different kinds of flavoring agents and dyes, to the base paste downstream of the vacuum mixer in a closed continuous proportioning system under pressure to prevent the entrainment of air. Thus different toothpaste products can be obtained using a common base paste. Moreover, by omitting the addition of the various adjuvant materials to the base paste, shut down time for the cleaning and maintenance of the vacuum mixer due to changes in toothpaste formulations is avoided.

The method according to the present invention is understood to be applicable to those situations or product formulations where an essentially gas-free, homogeneous paste is desired. For the purposes of the invention herein, therefore, a paste can be defined as a viscous dispersion of finely divided, insoluble solids or powders suspended in a liquid medium.

EXAMPLE 7

A 500 pound batch of a hard surface cleaner composition was prepared having the following formula:

| Ingredients | Weight Percent |
|---|---|
| Water | 23.5 |
| 80/20 Tallow/coconut soap | 0.7 |
| Sodium alkyl ($C_{10}$–$C_{12}$) benzene sulfonate | 4.0 |
| Lauric diethanol amide | 2.4 |
| Premix A |  |
| Water | 4.0 |
| Aluminum Magnesium Silicate (Attagel-40) | 0.5 |
| Premix B |  |
| Water | 11.0 |
| Sodium tripolyphosphate | 4.8 |
| $CaCO_3$ | 36.0 |
| Koalinite | 12.0 |

| Ingredients | Weight Percent |
| --- | --- |
| NH₃ | 0.2 |
| | 100.0% |

The above formulation was prepared in accordance with the method of the invention as follows. About 23 percent water was charged to a Day Co. Nauta Vacuum Mixer, Model MBX-70 and heated to 160° F. The soap, sulfonate and lauric diethanol amide were then added, and the mixer actuated to blend the ingredients. Premixes A and B were added and the temperature of the contents cooled to 95° F. while the mixing continued. Finally the NH₃ was blended into the mixer contents.

A vacuum of 25 inches Hg. was drawn on the mixer contents while the mixing continued followed by the addition of the finely divided CaCO₃ and Kaolinite, in that order. The powders were drawn into the liquid mix at the bottom of the mixing chamber in the vicinity of the turbine impeller. Mixing and vacuuming continued for 20 minutes while maintaining the temperature of the mixture at 95° F. The vacuum was discontinued and the NH₃ added to the tank while mixing.

A smooth, deaerated product was obtained having a viscosity of 4500 centipoises.

The examples set forth above are given to illustrate the features of the method according to the present invention, and it is understood that the scope of the invention is not to be limited thereto.

What is claimed is:

1. A method for rapidly dispersing and wetting solids in a liquid medium to form an essentially gas free mixture comprising:
   (a) charging said liquid medium to a mixing tank;
   (b) subjecting said medium to intimate turbulent mixing and continuous vacuum; and
   (c) drawing said solids into said tank under the surface of said liquid medium by means of said vacuum into an area of highly turbulent mixing whereby simultaneously degassing, wetting and dispersing said solids.

2. A method as defined in claim 1 wherein said solids are insoluble.

3. A method as defined in claim 2 wherein said solids are dentifrice polishing and bodying agents.

4. A method as defined in claim 3 wherein said liquid medium includes a humectant, stabilizing agent and water.

5. A method as defined in claim 1 further comprising the steps of:
   (a) preparing a degassified detergent solution in a separate container; and
   (b) withdrawing the essentially gas-free mixture and detergent solution from the mixing tank and container, respectively, and combining the two mixtures under pressure in the absence of air to prevent entrainment of air therein.

6. A method as defined in claim 4 wherein the humectant is a polyhydric alcohol, the stabilizing agent is sodium carboxymethylcellulose, and the insoluble solids comprise a mixture of silica xerogel and silica aerogel.

7. A method as defined in claim 5 wherein the detergent solution contains a mixture of sodium lauryl sulfate, glycerine and ethanol.

* * * * *